United States Patent
Nakajima et al.

(10) Patent No.: US 11,783,930 B2
(45) Date of Patent: Oct. 10, 2023

(54) INFORMATION PROCESSING DEVICE, METHOD, AND NON-TRANSITORY COMPUTER-READABLE STORAGE MEDIUM STORING PROGRAM

(71) Applicant: OMRON HEALTHCARE Co., Ltd., Kyoto (JP)

(72) Inventors: Hiroshi Nakajima, Kyoto (JP); Hirotaka Wada, Kyoto (JP); Tamio Ueda, Kyoto (JP); Daisuke Nozaki, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 356 days.

(21) Appl. No.: 16/906,538

(22) Filed: Jun. 19, 2020

(65) Prior Publication Data

US 2020/0321093 A1    Oct. 8, 2020

Related U.S. Application Data

(63) Continuation of application No. PCT/JP2018/046251, filed on Dec. 17, 2018.

(30) Foreign Application Priority Data

Dec. 28, 2017  (JP) ................. 2017-253089

(51) Int. Cl.
*G16H 20/10* (2018.01)
*G16H 20/30* (2018.01)
(Continued)

(52) U.S. Cl.
CPC ............. *G16H 20/10* (2018.01); *G06Q 30/02* (2013.01); *G16H 10/60* (2018.01); *G16H 20/30* (2018.01); *G16H 20/60* (2018.01); *G16H 20/70* (2018.01)

(58) Field of Classification Search
CPC ........ G16H 20/10; G16H 10/60; G16H 20/30; G16H 20/60; G16H 20/70; G16H 40/63;
(Continued)

(56) References Cited

U.S. PATENT DOCUMENTS

2007/0055551 A1* 3/2007 Szabo ................... G16H 10/60
                                                              705/3
2008/0065413 A1  3/2008 Taniike et al.
(Continued)

FOREIGN PATENT DOCUMENTS

| JP | 2014-038432 A | 2/2014 |
| JP | 2017-123191 A | 7/2017 |
| WO | 2006/098298 A1 | 9/2006 |

OTHER PUBLICATIONS

International Search Report of the International Searching Authority for PCT/JP2018/046251 dated Feb. 12, 2019.
(Continued)

*Primary Examiner* — Pei Yong Weng
(74) *Attorney, Agent, or Firm* — Birch, Stewart, Kolasch & Birch, LLP

(57) ABSTRACT

The present invention effectively provides, to a user, a coupon to improve a lifestyle. An information processing device includes an acquisition unit configured to acquire user data including at least one of vital data including biological information pertaining to a user and lifestyle data pertaining to the user, a provision unit configured to apply, to the user data, reference data indicating criteria for determining a content of the user data and, in accordance with a result of the reference data being thus applied, provide, to the user, coupon data pertaining to a coupon configured to
(Continued)

encourage the user to take a specific action, and a determination unit configured to determine, on the basis of usage history data of the coupon data thus provided and the user data corresponding to the usage history data, whether or not a coupon corresponding to the usage history data is effective in improving a lifestyle of the user.

20 Claims, 8 Drawing Sheets

(51) Int. Cl.
*G16H 10/60* (2018.01)
*G16H 20/60* (2018.01)
*G16H 20/70* (2018.01)
*G06Q 30/02* (2023.01)

(58) Field of Classification Search
CPC ........ G16H 50/30; G06Q 30/02; A61B 5/318; A61B 5/01; A61B 5/021; A61B 5/02438; A61B 2503/12
See application file for complete search history.

(56) References Cited

U.S. PATENT DOCUMENTS

| | | | |
|---|---|---|---|
| 2008/0103910 A1* | 5/2008 | Gardenswartz | G06Q 30/02 705/14.27 |
| 2012/0041767 A1 | 2/2012 | Hoffman et al. | |
| 2013/0030879 A1* | 1/2013 | Munjal | G06Q 30/0635 705/7.42 |
| 2015/0134347 A1* | 5/2015 | Faurie | A61B 5/157 600/573 |
| 2016/0063569 A1 | 3/2016 | Williams | |

OTHER PUBLICATIONS

English translation of International Search Report of the International Searching Authority for PCT/JP2018/046251 dated Feb. 12, 2019.
International Preliminary Report on Patentability and English translation of the Written Opinion of the International Searching Authority (Forms PCT/IB/338, PCT/IB/373 and PCT/ISA/237) for Application No. PCT/JP2018/046251, dated Jul. 9, 2020.
Chinese Office Action and Search Report for Chinese Application No. 201880077401.3, dated Mar. 23, 2023, with an English translation.

* cited by examiner

INFORMATION PROCESSING DEVICE, METHOD, AND NON-TRANSITORY COMPUTER-READABLE STORAGE MEDIUM STORING PROGRAM

CROSS-REFERENCE TO RELATED APPLICATIONS

This is a continuation of International Application 2017-253089 with an international filing date of Dec. 28, 2017, and International Application PCT/JP2018/046251, with an international filing date of Dec. 17, 2018, filed by applicant, the disclosure of which is hereby incorporated by reference in its entirety.

TECHNICAL FIELD

This invention relates to an information processing device, a method, and a non-transitory computer-readable storage medium storing a program for issuing a coupon.

BACKGROUND ART

As a means for encouraging users to receive a specific product or service, a coupon issued by a service provider is generally well known.

In particular, there is a technology in which a coupon is delivered on the basis of information of a living body of a user (hereinafter also referred to as biological information).

For example, JP 2014-38432 A discloses a technology in which a type and a content of a coupon to be delivered are selected on the basis of a result of measuring a sample originating from a living body, such as exhaled breath or saliva. According to JP 2014-38432 A, the user attaches or carries a biological information detection device configured to detect a physical condition or a state of a body of the user, a sample originating from the living body, such as exhaled breath, saliva, sweat, or gas released from the skin is measured periodically or at a desired timing, and the measurement result and the measurement time are stored in a server on a network. Then, in JP 2014-38432 A, the measurement result and a predetermined threshold value are compared or reference is made to a transition in the measurement result, thereby making it possible to estimate the physical condition and the state of the body of the user and select and deliver the type and the content of a coupon considered optimal.

SUMMARY OF INVENTION

However, in the system disclosed in JP 2014-38432 A, the physical condition and the state of the body of the user are just used in processing for selecting a coupon, and whether or not the physical condition and the state of the body of the user improved by the user having used the delivered coupon is not determined. In this case, whether or not the coupon delivered on the basis of the biological information of the user contributed to improving the physical condition and the state of the body of the user cannot be confirmed.

Accordingly, JP 2014-38432 A is problematic in that whether or not a coupon delivered on the basis of the biological information of the user acted so as to optimize an amount indicated by the biological information of the user to an appropriate value cannot be determined. Thus, it is unclear whether or not the coupon was effective in improving the lifestyle of the user, and a coupon cannot be effectively provided to the user.

This invention has been made with reference to the above circumstances, and an object thereof is to provide an information processing device, a method, and a non-transitory computer-readable storage medium storing a program capable of effectively providing, to a user, a coupon to improve a lifestyle of the user.

In order to solve the problems described above, the present disclosure adopts the following configuration.

That is, an information processing device according to a first aspect of the present disclosure includes an acquisition unit configured to acquire user data including at least one of vital data including biological information pertaining to a user and lifestyle data pertaining to the user, a provision unit configured to apply, to the user data, reference data indicating criteria for determining a content of the user data and, in accordance with a result of the reference data being thus applied, provide, to the user, coupon data pertaining to a coupon configured to encourage the user to take a specific action, and a determination unit configured to determine, on the basis of usage history data of the coupon data thus provided and the user data corresponding to the usage history data, whether or not a coupon corresponding to the usage history data is effective in improving a lifestyle of the user.

In the configuration described above, the user data including at least one of vital data including the biological information pertaining to the user (that is, information of a living body pertaining to the user) and the lifestyle data pertaining to the user are acquired. Then, the reference data indicating the criteria for determining the content of the user data are applied to the user data. Then, on the basis of the result of the reference data being thus applied, coupon data pertaining to a coupon configured to encourage the user to take a specific action are provided to the user. Thus, the user can receive a coupon referenced by the reference data and presumed to lead to improvement in the lifestyle (or health state) of the user in accordance with the content of the user data. Furthermore, the determination unit is configured to refer to the usage history data of the coupon and determine from the corresponding user data whether or not use of the coupon is effective in improving the lifestyle of the user. Therefore, the effectiveness of the coupon provided to the user is determined, making it possible to determine which coupon is effective for the user. Accordingly, it is possible to provide an information processing device capable of effectively giving a coupon to a user to improve the lifestyle of the user.

The information processing device described above according to a second aspect further includes an updating unit configured to update a weight factor indicating a degree of association between a coupon determined to be effective in improving a lifestyle and the vital data and/or the lifestyle data corresponding to the coupon by increasing the weight factor.

In the configuration described above, the weight factor indicating the degree of association between a coupon determined to be effective in improving the lifestyle of the user and the vital data and/or the lifestyle data corresponding to this coupon is updated by increasing the weight factor, and thus it is expected that the greater the weight factor of the coupon, the greater the improvement in the lifestyle indicated by the corresponding vital data and/or lifestyle data. Accordingly, to improve a specific lifestyle, as long as, from among the coupons corresponding to the vital data and/or lifestyle data corresponding to this lifestyle, a coupon having a greater weight factor is provided to the user, a greater effect in improving a lifestyle can be expected.

In the information processing device described above according to a third aspect, the determination unit is configured to determine that the coupon was effective in a case where a variation amount, varied to an amount reflecting an effect of improving a lifestyle, in an amount indicated by the vital data and/or the lifestyle data, before and after coupon use, is greater than a threshold value.

In the configuration described above, whether or not the coupon was effective for the user is determined by comparing the amounts indicated by the corresponding vital data and/or lifestyle data before and after the coupon was used, and comparing that variation amount to a threshold value set in advance. However, this variation amount is an amount in a case where the variation is in a direction in which the effect of improving a lifestyle increases. With this threshold value appropriately set, a coupon from which a lifestyle improvement effect can be expected can be readily found. Further, the effect of the coupon can be appropriately determined by setting this threshold value for each category of the user data (for example, blood pressure, pulse, body temperature, food intake, exercise, and sleep).

In the information processing device described above according to a fourth aspect, the vital data include at least one of blood pressure data, pulse data, body temperature data, weight data, and electrocardiogram data.

In the configuration described above, it is possible to provide, to the user, coupon data pertaining to a coupon configured to encourage the user to take a specific action on the basis of the data of at least one of blood pressure, pulse, body temperature, weight, and electrocardiogram. Further, it is possible to determine whether or not the coupon is effective in improving the lifestyle of the user on the basis of the data of at least one of blood pressure, pulse, body temperature, weight, and electrocardiogram.

In the information processing device described above according to a fifth aspect, the lifestyle data include at least one of intake data indicating food consumed and an intake amount of food, exercise data indicating an exercise amount, sleep data indicating a sleep amount, smoking data indicating a smoking amount, medication data of medicine taken, food intake speed data indicating a speed of food intake, and periodontal disease data.

In the configuration described above, it is possible to provide, to the user, coupon data pertaining to a coupon configured to recommend a specific action to the user on the basis of the data of at least one of food intake, exercise, sleep, smoking, medication, food intake speed, and periodontal disease. Further, it is possible to determine whether or not the coupon is effective in improving the lifestyle of the user on the basis of the data of at least one of food intake, exercise, sleep, smoking, medication, food intake speed, and periodontal disease.

In the information processing device described above according to a sixth aspect, the reference data include data including one or more threshold values configured to give meaning to the user data.

In the configuration described above, the user data include one or more threshold values, and therefore the user data can be classified into at least two types per one reference data by a threshold value. Thus, the user data can be classified in detail on the basis of numerous types of reference data. As a result, the improvement in the lifestyle of the user can be analyzed in a multifaceted manner, making it possible to provide a wide variety of coupons to the user.

In the information processing device described above according to another aspect, the information of the living body is acquired by a biological information acquisition device attached to the user.

In the configuration described above, the biological information acquisition device is attached to the user, and thus it is possible to acquire the biological information from the user at any time in real-time.

According to the present invention, it is possible to provide an information processing device, a method, and a non-transitory computer-readable storage medium storing a program capable of effectively providing, to a user, a coupon to improve a lifestyle.

DESCRIPTION OF EMBODIMENTS

An embodiment according to an aspect of the present invention (hereinafter, also referred to as "the present embodiment") will be described below with reference to the drawings. Note that, in the following embodiment, parts denoted by the same reference numbers perform the same operations, and a repetitive explanation will be omitted.

Application Example

Figure 1:
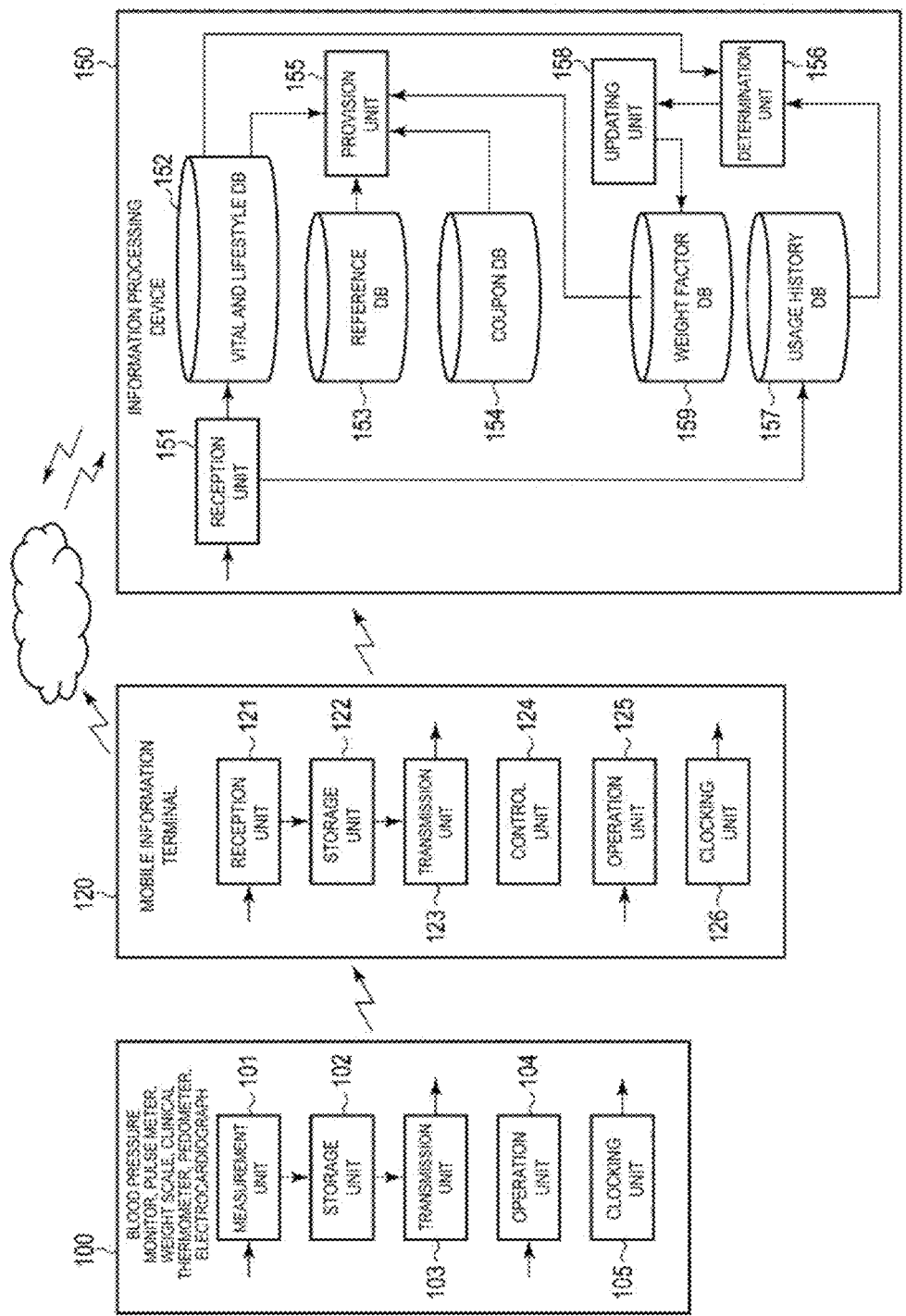
FIG. 1 is a drawing schematically illustrating an example of an application scenario of an information processing device, a biological information acquisition device, and a mobile information terminal according to an embodiment.

First, with reference to FIG. 1, an example of a scenario in which the present invention is applied will be described. FIG. 1 schematically illustrates an example of an application scenario of a biological information acquisition device 100, a mobile information terminal 120, and an information processing device 150 according to the present embodiment. In the biological information acquisition device 100 according to the present embodiment, a measurement unit 101 measures an amount pertaining to biological information from a living body, a storage unit 102 stores data indicating this measured amount, and a transmission unit 103 transmits these stored data to the mobile information terminal 120. Further, an operation unit 104 receives an operation of the user, and a clocking unit 105 provides a date and a time to each unit or the user. Here, the biological information is vital data obtained from the living body of the user. The vital data are data including an indicator indicating that a person is living, including, for example, a blood pressure value, a pulse value, a weight, a body temperature, a step count, and an electrocardiogram. Accordingly, the biological information acquisition device 100 is, for example, a blood pressure monitor, a pulse meter, a weight scale, a clinical thermometer, a pedometer, and/or an electrocardiograph.

Then, the mobile information terminal 120 mediates communication between the biological information acquisition device 100 and the information processing device 150. A reception unit 121 receives the vital data from the biological information acquisition device 100, a storage unit 122 stores the vital data, and a transmission unit 123 transmits the stored vital data to the information processing device 150. An operation unit 125 receives an operation of the user, and a clocking unit 126 provides the date and the time to each unit or the user. Further, a control unit 124 executes a program stored in the storage unit 122 and controls the mobile information terminal 120. The mobile information terminal 120 is, for example, a mobile terminal such as a smart phone, a mobile phone, or a mobile personal computer, or server.

Further, the mobile information terminal 120 acquires, from the user, lifestyle data pertaining to a lifestyle of the user. The mobile information terminal 120 asks the user questions pertaining to his or her lifestyle, for example, and acquires the lifestyle data on the basis of the answers. The lifestyle data are data pertaining to the lifestyle of the user other than the vital data. The lifestyle data are data including at least one of intake data indicating food consumed by the user, exercise data indicating an amount of exercise performed by the user, sleep data indicating a sleep amount of the user, smoking data indicating a smoking amount of the user, medication data of medicine taken by the user, food intake speed data indicating a speed of food intake by the user, and periodontal disease data of the user, for example. Note that the term food is a generic term for items consumed as foodstuffs, and also includes drink.

In the information processing device 150 according to the present embodiment, a reception unit 151 receives the vital data and the lifestyle data from the mobile information terminal 120. A vital and lifestyle database (abbreviated as DB) 152 stores the vital data and the lifestyle data.

The vital and lifestyle DB 152 stores, for example, the vital data and the lifestyle data along with date data associated with the data. Note that the information processing device 150 according to the present embodiment is equivalent to the "information processing device" of the present invention.

A reference DB 153 stores reference data indicating criteria for determining a content corresponding to a meaning of an amount indicated by the individual data included in the vital data and the lifestyle data. The reference data typically include a threshold value configured to give meaning to the data. As an example, as the reference data in the case of the blood pressure data within the vital data, the content "determine that the user has hypertension if systolic blood pressure is 140 mmHg or higher or diastolic blood pressure is 90 mmHg or higher", for example, is converted into data.

In this case, the reference data include two threshold values: "systolic blood pressure 140 mmHg" and "diastolic blood pressure 90 mmHg". Further, as the reference data in the case of the intake data within the lifestyle data, the content "determine that the user has best food intake if the food consumed in one day includes 30 items or more and is distributed across all food groups from group 1 to group 6" and "determine that the user has insufficient food intake if the food consumed in one day includes 30 items or more, but the food intake of group 3 (green and yellow vegetables) of the food groups, upon comparison with the other food groups, is 3 or more items less than the other food groups", for example, is converted into data. In this case, the reference data include three threshold values: "30 items", "all groups from group 1 to group 6", and "food intake of group 3 of the food groups, upon comparison with the other food groups, is 3 or more items less than the other food groups".

These reference data may be stored in the reference DB 153 in advance or, each time there is an addition to or a change in the data stored in the vital and lifestyle DB 152, the reference data corresponding to the data may be automatically retrieved and acquired from a network. Note that desirably one or more reference data are stored in the reference DB 153 per one data stored in the vital and lifestyle DB 152.

A coupon DB 154 stores coupon data of coupons configured to encourage the user to take a specific action. The coupon data include, for example, the content "a complimentary ticket allowing preferential treatment at a clinic" converted into data. This coupon is provided to the user in a case where, for example, the user is determined to have hypertension. Further, the coupon data include, for example, the content "discount coupon for purchasing food corresponding to group 3 (green and yellow vegetables) of the food groups" converted into data. This coupon is provided to the user in a case where, for example, the user has significantly less intake of green and yellow vegetables compared to the other food groups. Note that, in general, desirably one or more coupon data are stored in the coupon DB 154 per one data stored in the vital and lifestyle DB 152.

A provision unit 155 applies the reference data stored in the reference DB 153 corresponding to the data stored in the vital and lifestyle DB 152, acquires the coupon data from the coupon DB 154 corresponding to a result of this application, and provides the coupon data to the user.

A usage history DB 157 stores history data of the coupons used by the user. A determination unit 156 compares a used coupon in the usage history DB 157 and the values indicated by the data in the vital and lifestyle DB 152 corresponding to the used coupon before and after coupon use to determine whether or not the coupon was effective for the user.

An updating unit 158 receives a determination result of the determination unit 156, and updates a weight factor indicating a degree of association between the coupon and the data stored in the vital and lifestyle DB 152 corresponding to this coupon. In a case where the determination unit 156 determines that the coupon is effective, the updating unit 158 increases the weight factor between the corresponding coupon and the data by a predetermined value. Conversely, in a case where the determination unit 156 determines that the coupon is not effective, the updating unit 158 decreases the weight factor between the corresponding coupon and the data by a predetermined value. Further, the updating unit 158 may change the value of the weight factor in accordance with a magnitude of the effect.

A weight factor DB 159 converts the weight factor indicating a degree of association between the coupon stored in the coupon DB 154 and the data stored in the vital and lifestyle DB 152 corresponding to this coupon into data, and stores the converted data. Note that the provision unit 155 refers to the data stored in the vital and lifestyle DB 152, the coupon data stored in the coupon DB 154 corresponding to these data, and the weight factor data associated therewith to select the coupon data. The provision unit 155 selects and provides to the user coupon data corresponding to the weight factor data having the greatest weight factor, for example. In general, one or more coupon data are stored in the coupon DB 154 per one data stored in the vital and lifestyle DB 152.

As described above, in the present application example, the information processing device 150 acquires the vital data acquired by the biological information acquisition device 100 and the lifestyle data acquired from the mobile information terminal 120, and applies corresponding reference data of the reference data stored in the reference DB 153 to the acquired data. In accordance with the result of this application, the provision unit 155 can select coupon data from the coupon DB 154 and provide a coupon corresponding to the coupon data to the user. Furthermore, the determination unit 156 records the usage history of the coupon provided to the user, and determines whether or not the values indicated by the vital data or the lifestyle data corresponding to the coupon used reflect an effect of improving a lifestyle before and after coupon use. In a case where the determination unit 156 determines that this coupon was effective in improving a lifestyle, the updating unit 158 updates the weight factor indicating the degree of association between this coupon and the corresponding vital data or lifestyle data by increasing the weight factor. As a result, a coupon that contributes to improving a lifestyle is more likely to be provided, making it possible to more effectively provide a coupon to the user that will lead to improvement in his or her lifestyle. Thus, according to the present application, it is possible to provide an information processing device capable of effectively providing, to a user, a coupon to improve the lifestyle of the user.

Configuration Example

Hardware Configuration
Information Processing Device

Next, an example of a hardware configuration of the information processing device 150 according to the present embodiment will be described using FIG. 2.

Figure 2:
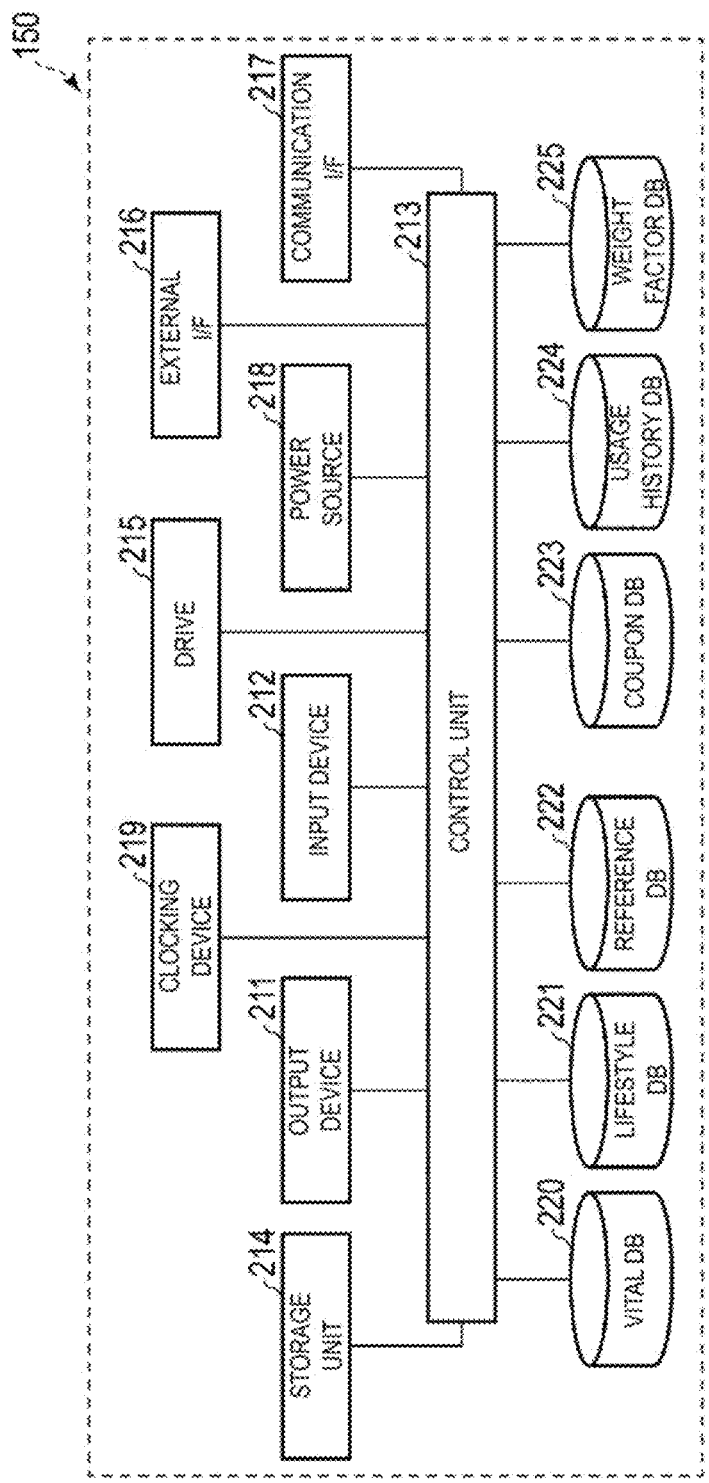
FIG. 2 is a drawing schematically illustrating an example of a hardware configuration of the information processing device according to an embodiment.

In the example in FIG. 2, the information processing device 150 according to the present embodiment may be a computer in which an output device 211, an input device 212, a control unit 213, a storage unit 214, a drive 215, an external interface 216, a communication interface 217, and a power source 218 are electrically connected. Furthermore, the information processing device 150 includes a clocking device 219, a vital DB 220, a lifestyle DB 221, a reference DB 222, a coupon DB 223, a usage history DB 224, and a weight factor DB 225. The information processing device 150 according to the present embodiment corresponds to the "information processing device" of the present invention. Note that the communication interface and the external interface are written as "communication I/F" and "external I/F", respectively, in FIG. 2 (hereinafter also written this way as well).

The control unit 213 includes a central processing unit (CPU), a random-access memory (RAM), a read-only memory (ROM), and the like, and controls each component in accordance with information processing. The storage unit 214 is, for example, an auxiliary storage device such as a hard disk drive or a solid state drive, and stores a program configured to optimize coupon selection (also referred to as an optimization program) executed by the control unit 213, acquisition data acquired from the mobile information terminal 120, image data to be transmitted, and the like.

The program configured to optimize coupon selection is a program for executing processing (FIG. 7) for selecting optimal coupon data on the basis of the user data, and providing the coupon data to the user. The acquired data acquired from the mobile information terminal 120 are the vital data and/or the lifestyle data.

The communication interface 217 may be any interface that communicates with the mobile information terminal 120 such as, for example, a wireless local area network (LAN) module, a wired LAN module, or a near-field wireless communication (for example, Bluetooth (trade name)) module, and is an interface configured to perform communication via a network or the like. The communication interface 217 is an interface configured to wirelessly connect the mobile information terminal 120 and the information processing device 150. The communication interface 217 is controlled by the control unit 213. The communication interface 217 receives data that serve as a source of symbol data from the mobile information terminal 120.

The communication interface 217 is used to receive image display data generated by the control unit 213 and transmit the data to the mobile information terminal 120.

The input device 212 is a device configured to perform input, such as a mouse or a keyboard, for example. The output device 211 is a device configured to perform output, such as a display or a speaker, for example. The external interface 216 is a USB port or the like, and is an interface configured to connect to an external device, such as the clocking device 219, the vital DB 220, the lifestyle DB 221, the reference DB 222, the coupon DB 223, the usage history DB 224, and/or the weight factor DB 225, for example. In FIG. 2 and the like, the clocking device 219, the vital DB 220, the lifestyle DB 221, the reference DB 222, the coupon DB 223, the usage history DB 224, and/or the weight factor DB 225 are not illustrated as connected to the external interface 216. This is because these databases are described as being directly connected to the control unit 213 for the sake of convenience in order to clarify connection with an internal block of the control unit 213 in FIG. 5 and the like later.

The storage unit 214 is a medium that stores information such as a recorded program by electrical, magnetic, optical, mechanical, or chemical action so that a computer or other device, a machine, or the like can read information such as the program. The information processing device 150 may acquire, from this storage unit 214, the program configured to optimize coupon selection, acquisition data acquired from the mobile information terminal 120, image data to be transmitted, and the like.

The drive 215 is, for example, a compact disc (CD) drive, a digital versatile disc (DVD) drive, or the like, and is a device configured to read a program stored in a storage medium. The type of the drive 215 may be selected as appropriate according to the type of the storage medium. The above-described optimization program, the acquisition data acquired from the mobile information terminal 120, and/or the image data to be transmitted may be stored in this storage medium. Here, as an example of a storage medium, a storage medium of a disk type, such as a CD or a DVD, is illustrated. Nevertheless, the type of storage medium is not necessarily limited to a disk type, and may be a type other than a disk type. Examples of a storage medium other than a disk type include a semiconductor memory such as flash memory. Note that the storage medium is a medium that stores information such as a recorded program by electrical, magnetic, optical, mechanical, or chemical action so that a computer or other device, a machine, or the like can read information such as the program.

The power source 218 is a device that supplies power to each element mounted to the body of the information processing device 150, and is, for example, a device that generates a constant voltage source. The power source 218 supplies power to, for example, the output device 211, the input device 212, the control unit 213, the storage unit 214, the drive 215, the external interface 216, the communication interface 217, the clocking device 219, the vital DB 220, the lifestyle DB 221, the reference DB 222, the coupon DB 223, the usage history DB 224, and the weight factor DB 225.

The clocking device 219 is a device configured to measure time, and can measure a date and a time. For example, the clocking device 219 is a clock that includes a calendar, and passes current date and time information to the control unit 213.

The vital DB 220 stores the vital data acquired from the mobile information terminal 120 and handled by the information processing device 150. The vital data may include date data in which data are acquired by the mobile information terminal 120.

The lifestyle DB 221 stores the lifestyle data acquired from the mobile information terminal 120.

The lifestyle data may include date data in which data are acquired by the mobile information terminal 120.

The reference DB 222 stores the reference data. The reference data may be set in advance for each of the vital data and the lifestyle data, or corresponding data retrieved outside the network or the like may be acquired. The reference data may be any data as long as the data makes it possible to determine a health state and/or a lifestyle status of the user on the basis of the vital data and/or the lifestyle data. The reference data typically include a threshold value to indicate a change in the state of the user at that value. There are one or more reference data per one vital data or the lifestyle data. That is, one user data may be determined from a plurality of the reference data. Specifically, for example, a plurality of the reference data can be applied to the blood pressure data, which is one of the vital data, to extract information found from this blood pressure data in an amount corresponding to the number of reference data.

The coupon DB 223 stores coupons acquired from the vital data and/or the lifestyle data on the basis of the information determined on the basis of the reference data. That is, the coupon DB 223 stores one or more coupons corresponding to information indicating the determined result. The coupon DB 223 desirably stores as many coupons as possible and secures types and amounts allowing provision of appropriate coupons to all users.

The usage history DB 224 stores, for each user, information pertaining to which coupons were acquired and which coupons were used. The usage history DB 224 may store, for example, the reason for and the date and time of acquisition of the coupon, the location and the date and time of coupon use, and the like. The usage history DB 224 records which coupons have been acquired and records the usage status of each coupon.

The weight factor DB 225 stores weight factor data indicating a degree of association between the acquired coupon and corresponding user data. The weight factor data indicate that the greater the weight factor, the greater the association between this coupon and the corresponding user data.

Note that, with respect to the specific hardware configuration of the information processing device 150, components can be omitted, substituted, and added as appropriate in accordance with the embodiment. For example, the control unit 213 may include a plurality of processors. The information processing device 150 may be constituted by a plurality of information processing devices. Further, the information processing device 150 may use a general-purpose desktop personal computer (PC), a tablet PC, or the like in addition to an information processing device dedicatedly designed for the provided service.

Mobile Information Terminal

Next, an example of a hardware configuration of the mobile information terminal 120 according to the present embodiment will be described using FIG. 3. The hardware configuration of the mobile information terminal 120 is substantially the same as that of the information processing device 150.

Figure 3:
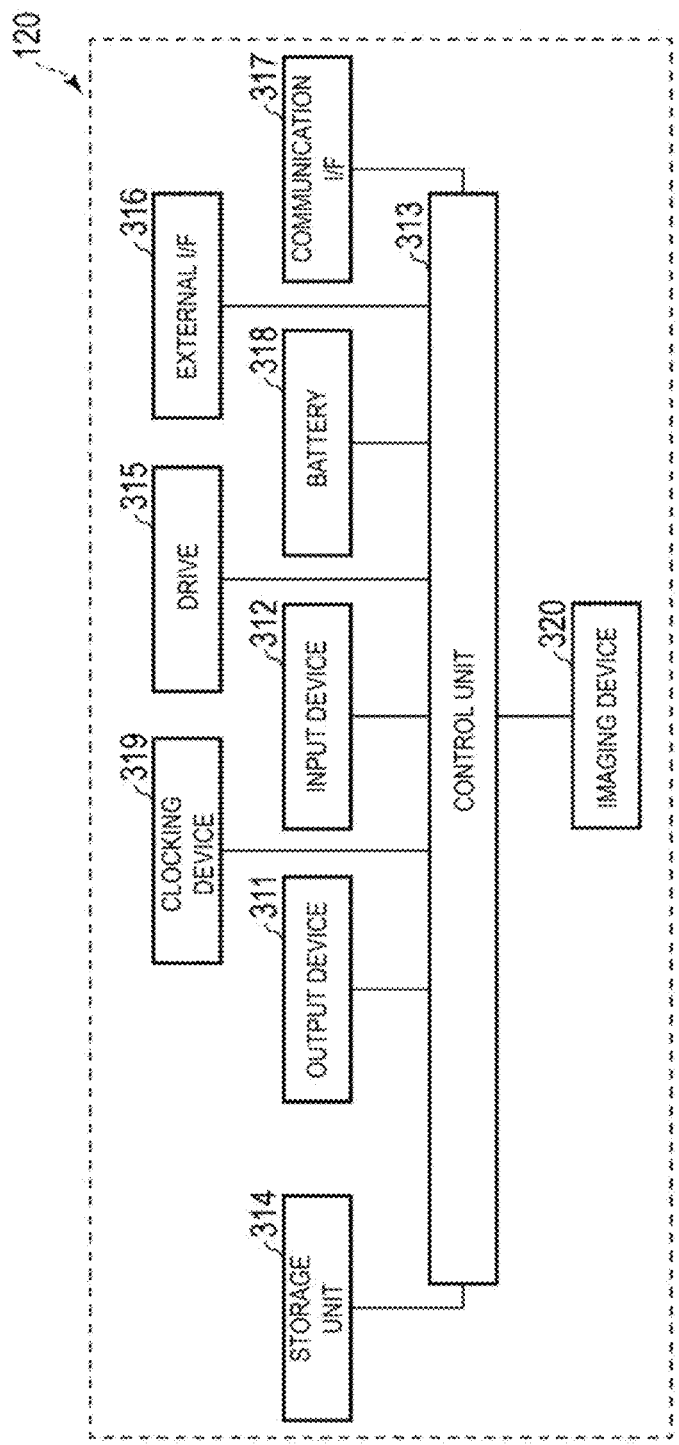
FIG. 3 is a drawing schematically illustrating an example of a hardware configuration of the mobile information terminal according to an embodiment.

As illustrated in FIG. 3, the mobile information terminal 120 according to the present embodiment may be a computer in which an output device 311, an input device 312, a control unit 313, a storage unit 314, a drive 315, an external interface 316, a communication interface 317, a battery 318, and a clocking device 319 are electrically connected. Furthermore, the mobile information terminal 120 includes an imaging device 320.

The control unit 313 includes a CPU, a RAM, a ROM, and the like, and controls each component in accordance with information processing. The storage unit 314 is, for example, an auxiliary storage device such as a hard disk drive or a solid state drive, and stores a captured image analysis program and an image display program executed by the control unit 313, acquisition data acquired from the mobile information terminal 120, display data received from the information processing device 150, and the like.

The captured image analysis program is a program configured to execute processing (FIG. 8) for analyzing an image captured by the imaging device 320 and acquiring information that can be acquired from the image. In the present embodiment, the program is, for example, a program configured to execute processing (FIG. 8) for capturing an image of food (that is. foodstuff and drink) and acquiring information such as calories, nutrients, and the like of the food. The image display program is a program configured to execute processing for displaying a coupon on a display of the output device 311 on the basis of display data (for example, imaged data of the coupon) generated by the information processing device 150.

The communication interface 317 is substantially similar to the communication interface 217. The communication interface 317 is an interface configured to receive data from the biological information acquisition device 100 and transmit and receive data to and from the information processing device 150. The communication interface 317 receives data from the biological information acquisition device 100 or the information processing device 150, passes the data to the control unit 313, receives transmission data for the information processing device 150 from the control unit 313, and transmits the transmission data.

The input device 312, the output device 311, and the external interface 316 are the same as the input device 212, the output device 211, and the external interface 216, respectively.

The storage unit 314 is a medium that stores information such as a recorded program by electrical, magnetic, optical, mechanical, or chemical action so that a computer or other device, a machine, or the like can read information such as the program. The mobile information terminal 120 may acquire, from this storage unit 314, the captured image analysis program, the image display program, the acquisition data acquired from the mobile information terminal 120, the display data received from the information processing device 150, and the like.

The drive 315 is, for example, a CD drive, a DVD drive, or the like, and is a device configured to read a program stored in a storage medium. The type of the drive 315 may be selected as appropriate according to the type of the storage medium. The above-described captured image analysis program, the image display program, the acquisition data acquired from the mobile information terminal 120, the display data received from the information processing device 150, and the like may be stored in this storage medium. Here, as an example of a storage medium, a storage medium of a disk type, such as a CD or a DVD, is illustrated. Nevertheless, the type of storage medium is not necessarily limited to a disk type, and may be a type other than a disk type. Examples of a storage medium other than a disk type include a semiconductor memory such as flash memory.

The battery 318 is, for example, a rechargeable secondary battery. The battery 318 supplies power to each element mounted to the body of mobile information terminal 120.

The clocking device 319 is similar to the clocking device 219.

The imaging device 320 is a device configured to capture an image of an object and acquire imaging data including the image, and is, for example, a digital camera. The imaging device 320 is typically equipped to a smart phone.

Note that, with respect to the specific hardware configuration of the mobile information terminal 120, components can be omitted, substituted, and added as appropriate in accordance with the embodiment. For example, the control unit 313 may include a plurality of processors. The mobile information terminal 120 may be constituted by a plurality of information processing devices. Further, the mobile information terminal 120 may use a general-purpose tablet PC or the like in addition to an information processing device dedicatedly designed for the provided service.

Biological Information Acquisition Device

Next, an example of a hardware configuration of the biological information acquisition device 100 according to the present embodiment will be described using FIG. 4. The hardware configuration of the biological information acquisition device 100 is substantially the same as that of the mobile information terminal 120.

Figure 4:
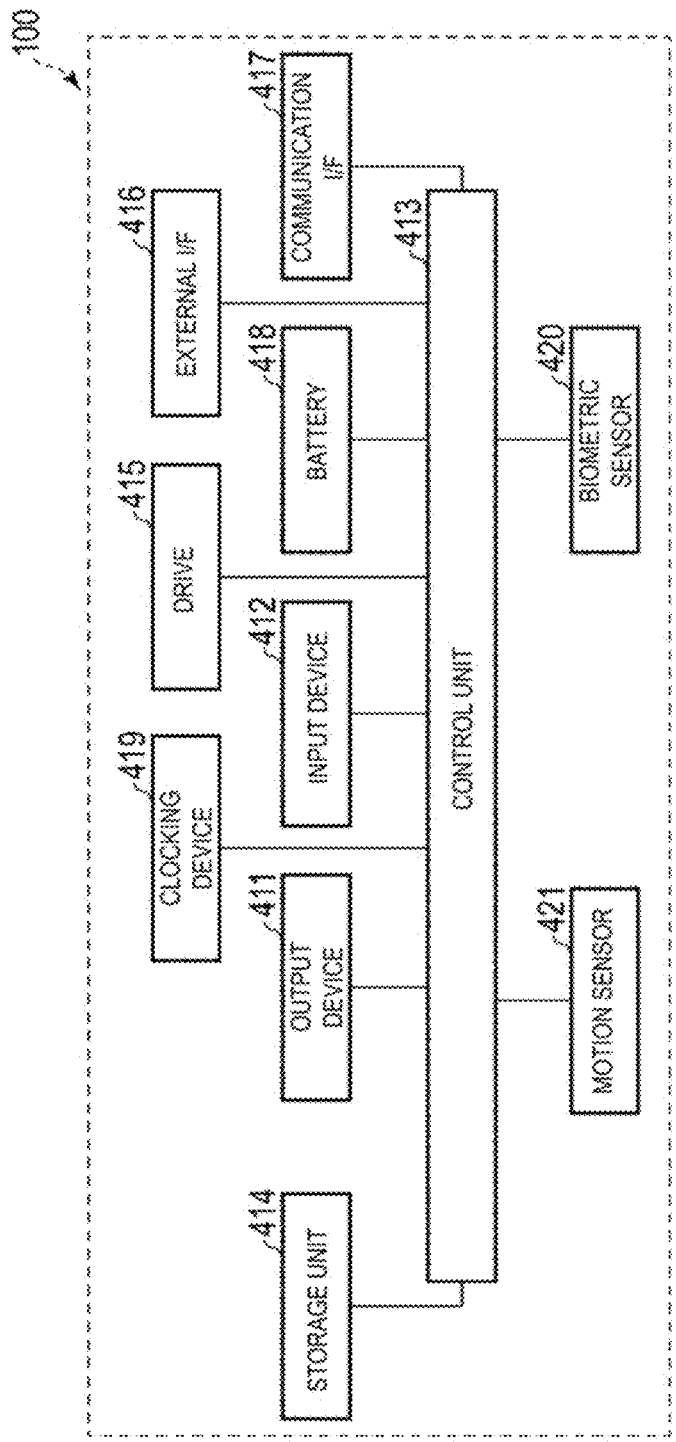
FIG. 4 is a drawing schematically illustrating an example of a hardware configuration of the biological information acquisition device according to an embodiment.

As illustrated in FIG. 4, the biological information acquisition device 100 according to the present embodiment may be a computer in which an output device 411, an input device 412, a control unit 413, a storage unit 414, a drive 415, an external interface 416, a communication interface 417, a battery 418, and a clocking device 419 are electrically connected. Furthermore, the biological information acquisition device 100 includes a biometric sensor 420 and a motion sensor 421.

The control unit 413 includes a CPU, a RAM, a ROM, and the like, and controls each component in accordance with information processing. The storage unit 414 is, for example, an auxiliary storage device such as a hard disk drive or a solid state drive, and stores a sensor data acquisition program executed by the control unit 413, acquisition data acquired from the mobile information terminal 120, sensor data detected by the biometric sensor 420 and/or the motion sensor 421, and the like.

The sensor data acquisition program is a program configured to acquire physical quantities detected by the biometric sensor 420 and/or the motion sensor 421 as data. In the present embodiment, the biometric sensor 420 is configured to acquire the vital data, and acquires, for example, blood pressure data and/or a pulse. The motion sensor 421 is configured to detect a motion of the biological information acquisition device 100, and is, for example, a three-axis acceleration sensor.

The communication interface 417 is substantially similar to the communication interface 317. The communication interface 417 is an interface configured to transmit data detected and acquired by the biological information acquisition device 100 to the mobile information terminal 120. The communication interface 417 may receive data from the mobile information terminal 120.

The input device 412, the output device 411, and the external interface 416 are the same as the input device 312, the output device 311, and the external interface 316, respectively.

The storage unit 414 is a medium that stores information such as a recorded program by electrical, magnetic, optical, mechanical, or chemical action so that a computer or other device, a machine, or the like can read information such as the program. The biological information acquisition device 100 may acquire the sensor data acquisition program from this storage unit 414.

The drive 415 is a device configured to read a program stored in a storage medium, and is, for example, a CD drive, a DVD drive, or the like. The type of the drive 415 may be selected as appropriate according to the type of the storage medium. The sensor data acquisition program described above may be stored in this storage medium. Here, as an example of a storage medium, a storage medium of a disk type, such as a CD or a DVD, is illustrated. Nevertheless, the type of storage medium is not necessarily limited to a disk type, and may be a type other than a disk type. Examples of a storage medium other than a disk type include a semiconductor memory such as flash memory.

The battery 418 is similar to the battery 318. The clocking device 419 is similar to the clocking device 319.

The biometric sensor 420 is configured to acquire the vital data, and is, for example, a blood pressure measurement device. In this case, for example, the biometric sensor 420 detects a pressure of a pressing cuff attached to a wrist of the user, which is a living body, to detect the blood pressure value of the living body. The biometric sensor 420 outputs blood pressure data (for example, time-series data of blood pressure values) to the control unit 213. Further, the biometric sensor 420 may also be a pulse measurement device, and pulse may be measured along with blood pressure.

The motion sensor 421 detects the motion of the living body and passes the motion information to the control unit 413. The motion sensor 421 is, for example, a three-axis acceleration sensor, and detects the acceleration of the living body with respect to three axes that are linearly independent (for example, three axes orthogonal to each other). Then, the motion sensor 421 outputs an acceleration signal indicating acceleration in three directions to the control unit 413.

Note that, with respect to the specific hardware configuration of the biological information acquisition device 100, components can be omitted, substituted, and added as appropriate in accordance with the embodiment. For example, the control unit 413 may include a plurality of processors. Further, the biological information acquisition device 100 may use a general-purpose tablet PC or the like in addition to an information processing device dedicatedly designed for the provided service.

Software Configuration
Information Processing Device

Figure 5:
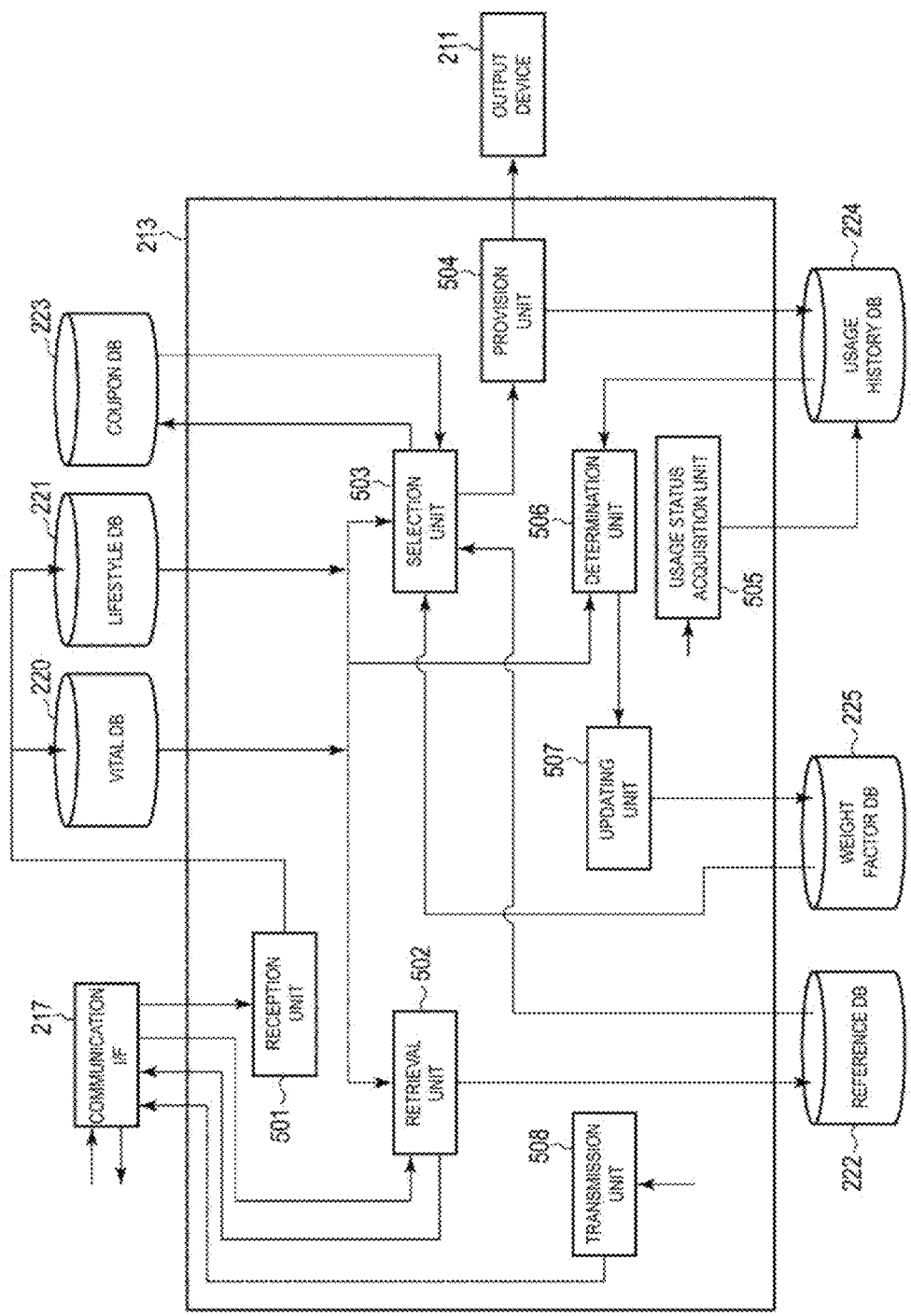
FIG. 5 is a drawing schematically illustrating an example of a software configuration of the information processing device according to an embodiment.

Next, an example of a software configuration of the information processing device 150 according to the present embodiment will be described using FIG. 5.

The control unit 213 of the information processing device 150 expands the program for optimizing coupon selection stored in the storage unit 214 in the RAM when a necessary program is to be executed. Then, the control unit 213 interprets and executes the optimization program expanded in the RAM by the CPU to control each component. Accordingly, as illustrated in FIG. 5, the control unit 213 of the information processing device 150 according to the present embodiment includes a reception unit 501, a retrieval unit 502, a selection unit 503, a provision unit 504, a usage status acquisition unit 505, a determination unit 506, an updating unit 507, and a transmission unit 508.

The reception unit 501 receives acquisition data acquired from the biological information acquisition device 100 by the mobile information terminal 120 via the communication interface 217. This acquisition data are user data (that is, the vital data and the lifestyle data described above) acquired by the biological information acquisition device 100, and is vital data including, for example, a blood pressure value, a pulse value, a weight, a body temperature, a step count, and an electrocardiogram, and lifestyle data including, for example, intake data indicating food consumed by the user, exercise data indicating an amount of exercise performed by the user, sleep data indicating a sleep amount of the user, smoking data indicating a smoking amount of the user, medication data of medicine taken by the user, food intake speed data indicating a speed of food intake by the user, and periodontal disease data of the user.

Further, the reception unit 501 may receive view request data pertaining to coupons from the mobile information terminal 120, transmit the data to the provision unit 504, and transmit usage history information acquired from the usage history DB 224 to the mobile information terminal 120 via the transmission unit 508. In addition, the reception unit 501 may receive, from the mobile information terminal 120, settings data for setting information related to the acquired data.

The retrieval unit 502 may search external sites on the basis of the vital data and the lifestyle data stored in the vital DB 220 and lifestyle DB 221, collect corresponding reference data, and store the reference data in the reference DB 222. Further, an administrator or the like of the information processing device 150 may store the reference data described above in advance in the reference DB 222.

The selection unit 503 applies the reference data from the reference DB 222 to the vital data from the vital DB 220 or the lifestyle data from the lifestyle DB 221, and selects coupon data from the coupon DB 223 in accordance with the application result. Further, the selection unit 503 passes the selected coupon data to the provision unit 504. The selection unit 503 may refer to the weight factor indicating the degree of association between the vital data and the lifestyle data, and the coupons (also referred to as "associated degree" or "association degree") to select one or more candidates for the coupon to be selected and, from among these candidates, and select the coupon data presumed optimal for the user in accordance with the application result. Further, the selection unit 503 may refer to the result of applying the reference data to the vital data and the lifestyle data, and weight factor indicating the degree of association with the coupons to select a coupon having a greater association degree.

The provision unit 504 provides, to the user, coupon data pertaining to the coupon selected by the selection unit 503. The provision unit 504, for example, outputs the coupon data to the output device 211. The output device 211 may output a coupon using a paper medium or the like to deliver the coupon to the user, or the coupon data may be transmitted to the mobile information terminal 120 via the transmission unit 508 and the communication interface 217 instead of the output device 211. In this case, the mobile information terminal 120 receives the coupon data, the user agrees to receive these coupon data, and the coupon data are stored in the mobile information terminal 120, making it possible for the user to use the coupon in accordance with the coupon data. Further, the provision unit 504 stores the type, the provision date and time, and the like of the coupon data provided to the user, in the usage history DB 224.

The usage status acquisition unit 505 acquires a usage status of the coupon of the user for each coupon provided by the provision unit 504, and stores data indicating the usage status of the coupon in the usage history DB 224. The usage status acquisition unit 505 acquires, for example, data indicating the coupons used and the location and time of use from the mobile information terminal 120 via the communication interface 217. In addition, the user may use the input device 212 to input the usage status of the coupon offline.

Further, a server device or the like configured to manage the coupons on the service providing side may observe the usage status of the coupon, and the usage status acquisition unit 505 may acquire the usage status data of the coupon from this server device or the like.

The determination unit 506, with reference to the usage history of the coupons stored in the usage history DB 224, compares the data stored in the vital DB 220 and/or the lifestyle DB 221 before and after coupon use, determines, for each coupon, whether or not the coupon is appropriate for the user who used the coupon, and passes the determination result together with the content to the updating unit 507. In a case where the coupon is a "complimentary ticket allowing preferential blood pressure treatment at a clinic", the determination unit 506 acquires and refers to systolic blood pressures and/or diastolic blood pressures before and after use of the coupon from the vital DB 220. Then, for example, in a case where, prior to use of this coupon, the blood pressure value indicated hypertension and, after use of the coupon, the blood pressure value returned to normal, the determination unit 506 determines that this coupon is effective for the user (appropriate for the user). The determination unit 506 may determine the degree of effectiveness by a time period until the blood pressure value returns to normal and/or a time period during which the normal value is sustained. For this degree of effectiveness, the determined time period varies depending on the content of the coupon, and thus the determination unit 506 conditions this time period on a per coupon basis.

Further, in a case where a plurality of coupons expected to be effective are used, the determination unit 506 may determine whether or not mutual interaction needs to be considered when these coupons are used in combination. For example, when a coupon for preferential hypertension treatment and a coupon allowing preferential attendance at an exercise gym for continual light exercise are used simultaneously, it is likely that the interpretation that there is a synergistic effect of the coupons is valid. Then, in a case where coupon use was effective in improving the symptoms of hypertension, it may be assessed that each of these coupons is effective in improving the symptoms of hypertension (each being, for example, 50% effective). On the other hand, in a case where the determination unit 506 determines that there is no interaction between the coupons, the effectiveness may be observed independently for each of the coupons. Whether or not there is interaction between coupons may be stored in advance in the coupon DB 223, or the user data that could possibly cause an interaction may be stored in association for each data stored in the vital DB 220 and the lifestyle DB 221. Note that desirably whether or not an interaction occurs, and if so, a rate of interaction, are determined on the basis of an established theory and/or experiment.

Furthermore, the determination unit 506 may analyze, from the plurality of data stored in the usage history DB 224, which coupon has a symptom improving effect on a certain symptom, and estimate a degree of contribution of each coupon when a plurality of coupons are used in combination. Alternatively, the degree of contribution of each coupon may be defined in advance and the determination unit 506 may determine the degree by referring thereto. For a pattern in which the degree of contribution of a coupon is not defined, the determination unit 506 may automatically estimate or have the user assess the degree of contribution.

The updating unit 507, on the basis of the determination result of the determination unit 506, updates the weight factor stored in the weight factor DB 225. The updating unit 507 updates the weight factor associated with the coupon corresponding to the determination result of the determination unit 506. This weight factor indicates the degree of association between a coupon and the vital data and/or the lifestyle data corresponding to the coupon. That is, the greater the weight factor, the stronger (denser) the association between the coupon and the vital data and/or the lifestyle data corresponding to this coupon. When the determination unit 506 determines that the coupon is appropriate for the user, the updating unit 507 updates the weight factor DB 225 by increasing the corresponding weight factor. On the other hand, when the determination unit 506 determines that the coupon is not appropriate for the user, the updating unit 507 updates the weight factor DB 225 by decreasing the corresponding weight factor.

The transmission unit 508 transmits the usage history data acquired from the usage history DB 224 and/or the coupon data provided by the provision unit 504 to the mobile information terminal 120.

Mobile Information Terminal

Figure 6:
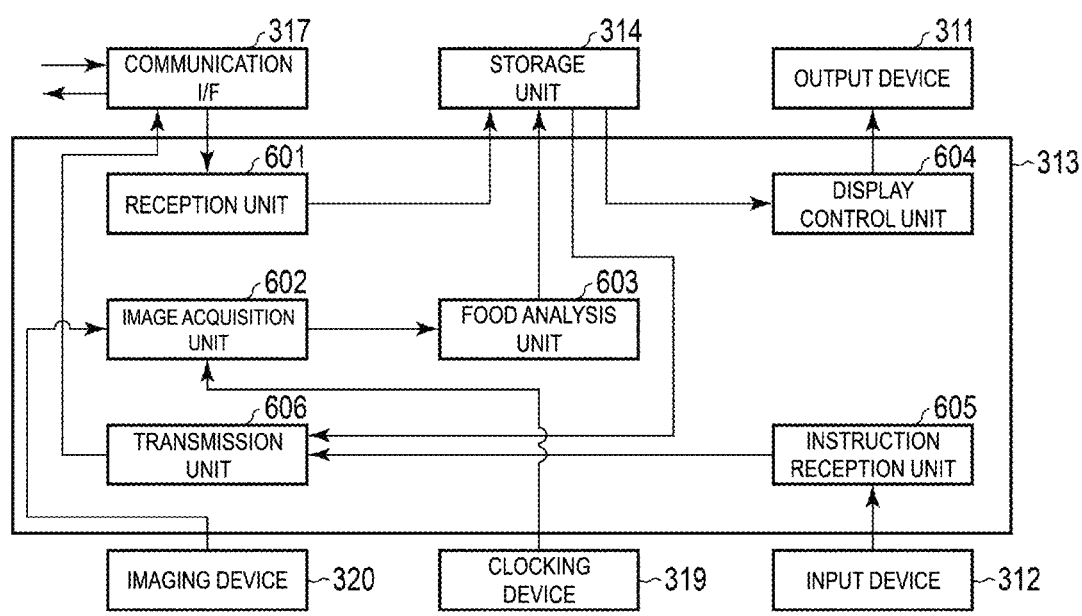
FIG. 6 is a drawing schematically illustrating an example of a software configuration of the mobile information terminal according to an embodiment.

Next, an example of a software configuration of the mobile information terminal 120 according to the present embodiment will be described using FIG. 6.

The control unit 313 of the mobile information terminal 120 expands the captured image analysis program and/or the image display program stored in the storage unit 314 in the RAM when a necessary program is to be executed. Then, the control unit 313 interprets and executes the captured image analysis program and/or the image display program expanded in the RAM by the CPU to control each component. Accordingly, as illustrated in FIG. 6, the control unit 313 of the mobile information terminal 120 according to the present embodiment includes a reception unit 601, an image acquisition unit 602, a food analysis unit 603, a display control unit 604, an instruction reception unit 605, and a transmission unit 606.

The reception unit 601 receives, from the biological information acquisition device 100, acquisition data acquired by the biological information acquisition device 100 via the communication interface 317. Further, the reception unit 601 receives, from the information processing device 150, image data corresponding to the view request data transmitted by the mobile information terminal 120 to the information processing device 150, via the communication interface 317. The acquisition data and the image data received by the reception unit 601 are stored in the storage unit 314.

The image acquisition unit 602 acquires imaging data including an image captured by the imaging device 320. The imaging device 320 captures an image of food, for example.

The food analysis unit 603 calculates, for example, contents of included nutrients (or amounts consumed by a human body) and calories of the food displayed by the imaging data by analyzing the imaging data acquired by the image acquisition unit 602. The image acquisition unit 602 may, for example, approximate the food and a size or a mass thereof from the imaging data, acquire information of the food from a database that exists in a network or the like, and calculate an intake amount of the nutrients and the calories of this food. Further, the transmission unit 606 may transmit the data captured by the image acquisition unit 602 to an external server device via the communication interface 317, and an analysis device included in the server device may perform the analysis performed by the food analysis unit 603.

The display control unit 604 acquires the image data and/or text data stored in the storage unit 314, and controls the data so as to cause the output device 311 to display an image and/or text on the basis of the corresponding data.

The instruction reception unit 605 receives an instruction from the user as instruction data via the input device 312. The instruction from the user may be, for example, a view request for data stored in the database (for example, "I want to view my blood pressure status for this month"), an instruction to check medicines taken, or an instruction to register information pertaining to medicine to be taken. The instruction reception unit 605 transmits the received instruction data to the transmission unit 606. The transmission unit 606 transmits the instruction data to the information processing device 150 via the communication interface 317.

Other

Each operation of the information processing device 150 and the mobile information terminal 120 are described in detail in the operation example described later. Note that, in the present embodiment, each of the components of the information processing device 150 and the mobile information terminal 120 may be realized by a general-purpose CPU. Nevertheless, a portion or all of the above functions may be realized by one or a plurality of dedicated processors. Further, with respect to the configuration of the information processing device 150 and/or the mobile information terminal 120 may be omitted, substituted, and added as appropriate in accordance with the embodiment.

Operation Example

Information Processing Device

Figure 7:
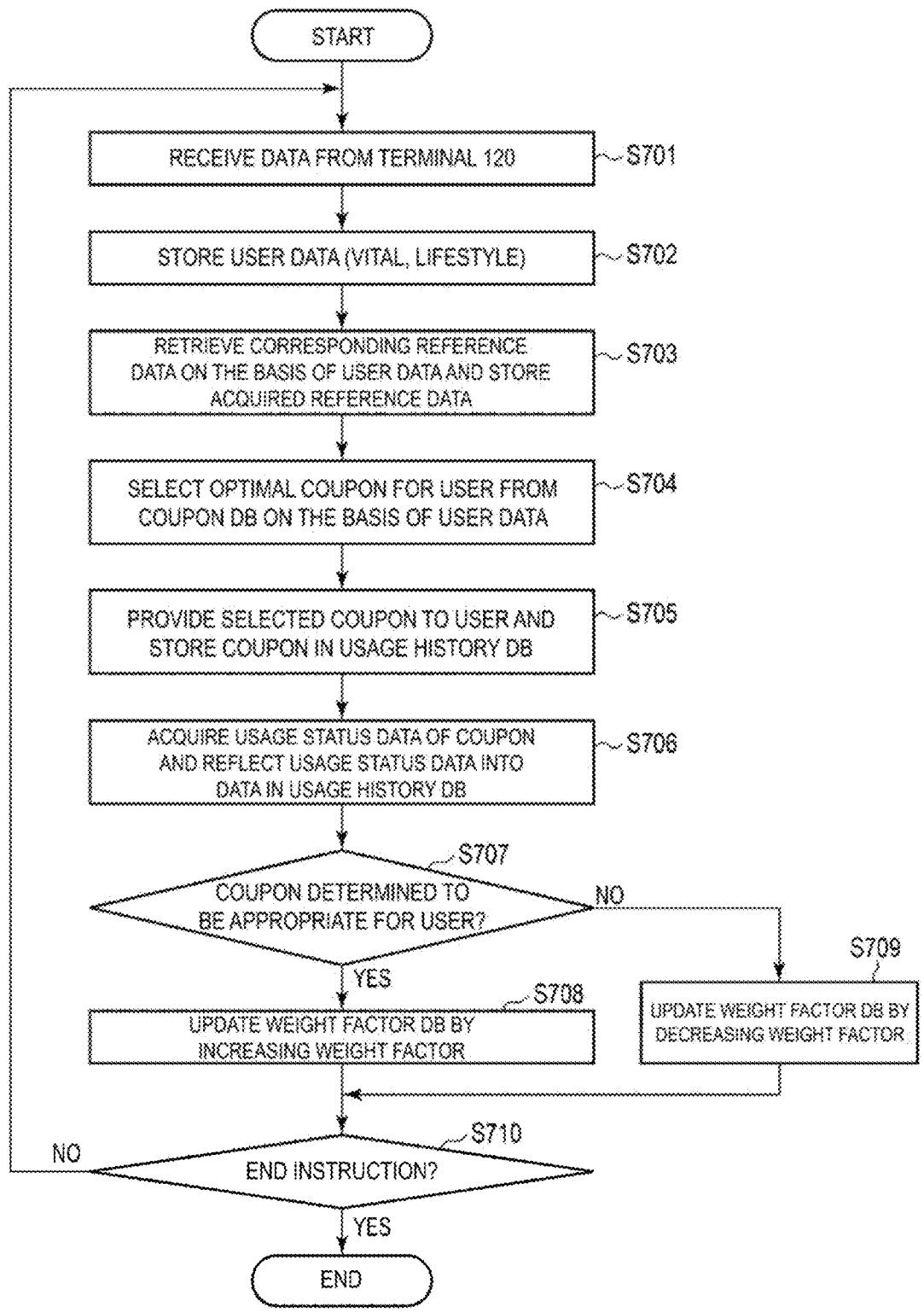
FIG. 7 is a drawing illustrating an example of a processing procedure of the information processing device according to an embodiment.

Next, an operation example of the information processing device 150 will be described using FIG. 7. FIG. 7 is a flowchart illustrating an example of a processing procedure of the information processing device 150. Note that the processing procedure described below is merely an example, and each process may be changed to the extent possible. Further, in the processing procedure described below, steps can be omitted, substituted, and added in accordance with the embodiment as appropriate.

Activation

First, the administrator activates the information processing device 150, causing the information processing device 150 thus activated to execute the program for optimizing coupon selection. The control unit 213 of the information processing device 150, in accordance with the processing procedure below, retrieves reference data on the basis of the user data, selects an optimal coupon for the user, updates the weight factor indicating the degree of association between the coupon and the user data, and optimizes coupon selection.

Step S701

In step S701, the control unit 213 operates as the reception unit 501 and receives the user data, which are data from the mobile information terminal 120 (also referred to as acquisition data). The user data are the vital data and/or the lifestyle data of the user.

Step S702

In step S702, the control unit 213 operates as the reception unit 501 and stores the vital data and the lifestyle data, which are the user data, in the vital DB 220 and the lifestyle DB 221, respectively.

Step S703

In step S703, the control unit 213 operates as the retrieval unit 502 and, from an external network, retrieves the corresponding reference data on the basis of the vital data stored in the vital DB 220 and the lifestyle data stored in the lifestyle DB 221. Then, the retrieval unit 502 stores the retrieved reference data in the reference DB 222 in association with the vital data and the lifestyle data.

Step S704

In step S704, the control unit 213 operates as the selection unit 503 and acquires the corresponding reference data from the reference DB 222 on the basis of the vital data stored in the vital DB 220 and the lifestyle data stored in the lifestyle DB 221.

Step S705

In step S705, the control unit 213 operates as the supply unit 504 and provides, to the user, a coupon selected by the selection unit 503, and stores the provided coupon data in the usage history DB 224.

Step S706

In step S706, the control unit 213 operates as the usage status acquisition unit 505, and the usage status acquisition unit 505 acquires the usage status data of the corresponding coupon from, for example, the mobile information terminal 120 and/or an external server device configured to manage coupon use, and reflects the usage status data into the data stored in the usage history DB 224.

Step S707

In step S707, the control unit 213 operates as the determination unit 506 and, with reference to the usage history data stored in the usage history DB 224 and the vital data and the lifestyle data, determines whether or not this coupon is appropriate for the user. In a case where it is determined that the coupon is appropriate for the user, the processing proceeds to step S708. On the other hand, in a case where it is determined that the coupon is not appropriate for the user, the processing proceeds to step S709.

Step S708

In step S708, the control unit 213 operates as the updating unit 507, and updates the weight factor DB 225 by increasing the weight factor stored by the weight factor DB 225. In a case where the weight factor is greater than or equal to a certain value, the updating unit 507 may not update the weight factor data in the weight factor DB 225.

Step S709

In step S709, the control unit 213 operates as the updating unit 507, and updates the weight factor DB 225 by decreasing the weight factor stored by the weight factor DB 225. In a case where the weight factor is less than a certain value, the updating unit 507 may not update the weight factor data in the weight factor DB 225. Further, in a case where the weight factor is less than a certain value, the updating unit 507 may set the corresponding weight factor to 0.

Step S710

In step S710, the control unit 213 operates as the reception unit 501 and determines whether or not an end instruction for ending processing has been received via the communication interface 217, for example. In a case where an end instruction has been received, the processing ends, and in a case where an end instruction has not been received, the processing returns to step S701 and the control unit 213 waits to receive data from the mobile information terminal 120. Further, for example, the control unit 213 may determine whether or not the input device 212 has received an end instruction from the administrator or the like of the information processing device 150.

Mobile Information Terminal

Figure 8:
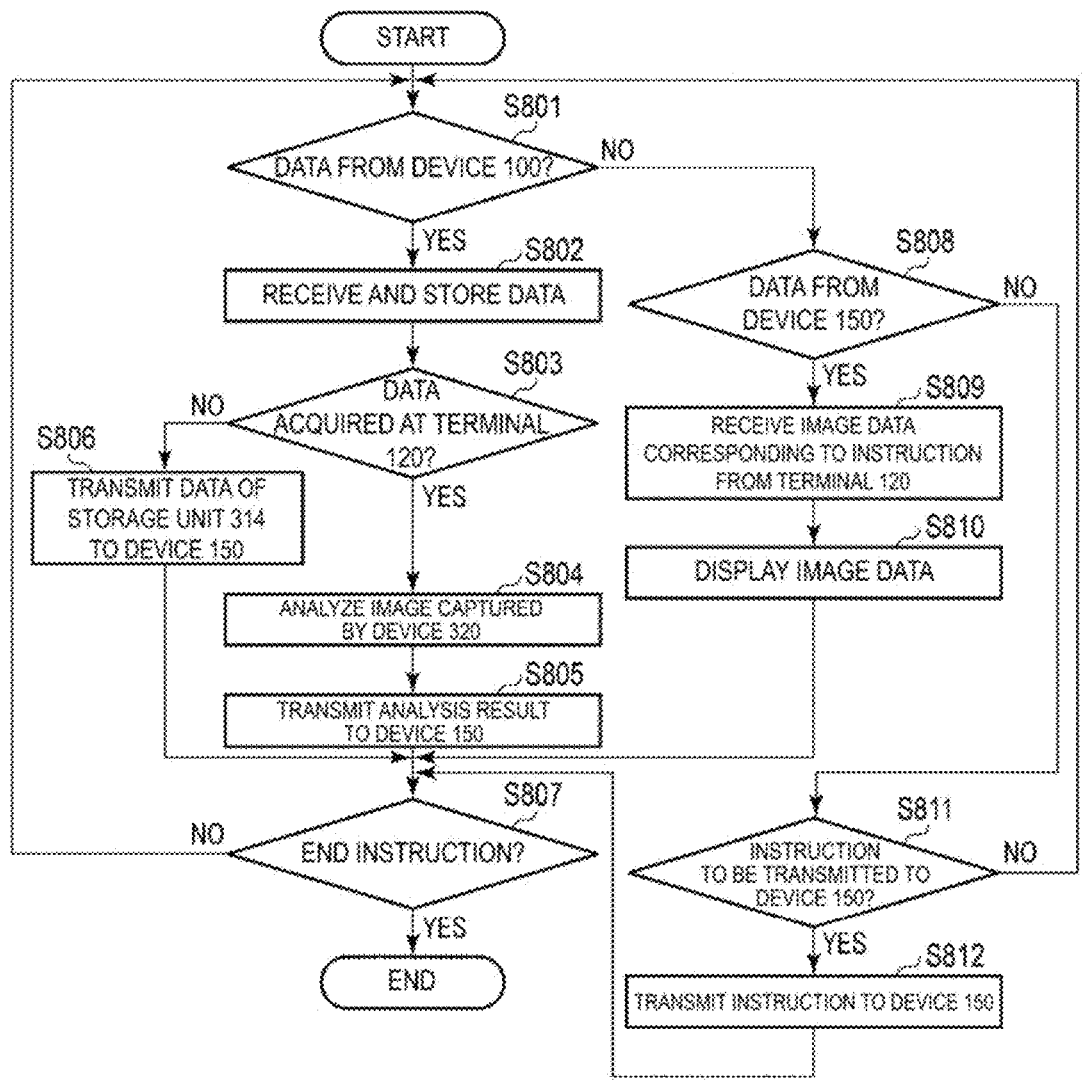
FIG. 8 is a drawing illustrating an example of a processing procedure of the mobile information terminal according to an embodiment.

Next, a description is given of an operation example of the mobile information terminal 120 using FIG. 8. FIG. 8 is a flowchart illustrating an example of a processing procedure of the mobile information terminal 120. Note that the processing procedure described below is merely an example, and each process may be changed to the extent possible. Further, in the processing procedure described below, steps can be omitted, substituted, and added in accordance with the embodiment as appropriate.

Activation

First, the user activates the mobile information terminal 120, causing the mobile information terminal 120 thus activated to execute the captured image analysis program and/or the image display program. The control unit 313 of the mobile information terminal 120, in accordance with the processing procedure below, transmits to the information processing apparatus 150 the result of acquiring and analyzing the image captured by the imaging device 320. Further, the control unit 313 transmits data received from the biological information acquisition device 100 to the information processing device 150. In addition, the control unit 313 transmits a view request signal for data stored in a database, for example, from the mobile information terminal 120 to the information processing device 150, receives the image data from the information processing device 150 in accordance with the request, and displays the corresponding image.

Step S801

In step S801, the control unit 313 operates as the reception unit 601, and determines whether or not the data received via the communication interface 317 are data received from the biological information acquisition device 100. In a case where the data received are data received from the biological information acquisition device 100, the processing proceeds to step S802, and in a case where the data received are not data received from the biological information acquisition device 100, the processing proceeds to step S808.

Step S802

In step S802, the control unit 313 operates as the reception unit 601, and stores the data received via the communication interface 317 in the storage unit 314.

Step S803

In step S803, the control unit 313 operates as the image acquisition unit 602, and determines whether or not there are image data captured by the imaging device 320 and acquired by the image acquisition unit 602.

Step S804

In step S804, the control unit 313 operates as the food analysis unit 603, analyzes the image data acquired by the image acquisition unit 602, and stores the image analysis result in the storage unit 314. The image acquisition unit 602 analyzes the image data of the food and calculates the nutrients and the calories.

Step S805

In step S805, the control unit 313 operates as the transmission unit 606, and transmits the stored analysis result data to the information processing device 150 via the communication interface 317.

Step S806

In step S806, the control unit 313 operates as the transmission unit 606, and transmits the stored data from the biological information acquisition device 100 to the information processing device 150 via the communication interface 317.

Step S807

In step S807, the control unit 313 operates as the instruction reception unit 605 and determines whether or not an end instruction from the user has been received via the input device 312. As another possibility, the control unit 313 may operate as the reception unit 601 and, upon receiving an end instruction from the information processing device 150 or the biological information acquisition device 100, end the processing. In a case where an end instruction is determined as having been received, the processing is ended, and in a case where an end instruction is determined as not having been received, the processing returns to step S801.

Step S808

In step S808, the control unit 313 operates as the reception unit 601, and determines whether or not the data received via the communication interface 317 are data received from the information processing device 150. In a case where the data received are data received from the information processing device 150, the processing proceeds to step S809, and in a case where the data received are not data received from the information processing device 150, the processing proceeds to step S811.

Step S809

In step S809, the control unit 313 operates as the reception unit 601, and receives image data in accordance with an instruction (for example, a view request instruction for viewing data) from the mobile information terminal 120.

Step S810

In step S810, the control unit 313 operates as the display control unit 604, and displays the image data received from the information processing device 150 on the output device 311.

Step S811

In step S811, the control unit 313 operates as the instruction reception unit 605 and the transmission unit 606, and determines whether or not there is an instruction to be transmitted to the information processing device 150. In a case where it is determined that there is an instruction to be transmitted, the processing proceeds to step S812, and in a case where it is determined that there is not an instruction to be transmitted, the processing returns to step S801.

Step S812

In step S812, the control unit 313 operates as the transmission unit 606, transmits the instruction data to the information processing device 150 via the communication interface 317, and proceeds to step S807.

Actions and Effects

As described above, in the present embodiment, in step S701 described above, the vital data acquired by the biological information acquisition device 100 and the lifestyle data acquired from the mobile information terminal 120 are acquired, and the corresponding reference data of the reference data stored in the reference DB 222 are applied to the acquired data. Then, in step S707, in accordance with the result of this application, the selection unit 503 can select coupon data from the coupon DB 223 and provide a coupon corresponding to the coupon data to the user. Furthermore, in step S705 to step S707, the determination unit 506 records the usage history of the coupon provided to the user in the usage history DB 224, and determines whether or not the values indicated by the vital data or the lifestyle data corresponding to the coupon used reflect an effect of improving a lifestyle before and after coupon use. In a case where the determination unit 506 determines that this coupon was effective in improving a lifestyle, the updating unit 507 updates the weight factor indicating the degree of association between this coupon and the corresponding vital data or lifestyle data by increasing the weight factor. As a result, a coupon that contributes to improving the lifestyle of the user is more likely to be provided, making it possible to more effectively provide a coupon to a user that will lead to improvement in his or her lifestyle. Thus, according to the present application, it is possible to effectively provide, to a user, a coupon to improve the lifestyle of the user.

Modified Examples

While embodiments of the present invention have been described in detail above, the foregoing description is merely illustrative of the present invention in all respects. Of course, various modifications and variations can be made without departing from the scope of the present invention. For example, the following changes are possible. Further, specific configurations according to the embodiment may be adopted as appropriate in the implementation of the invention. Note that, in the following, the same reference numerals are used for components similar to those of the above-described embodiment, and descriptions thereof will be omitted as appropriate. The following modified examples can be combined as appropriate.

The mobile information terminal 120 is configured separately from the biological information acquisition device 100. Nevertheless, the configuration of the biological information acquisition device 100 and the mobile information terminal 120 need not be limited to such an example, and a system having the functions of both the biological information acquisition device 100 and the mobile information terminal 120 may be realized by one computer.

The device of the present invention may also be realized by a computer and a program, and the program may be recorded in a recording medium (or storage medium), or provided through a network.

Further, the above-described devices and the device portions thereof can each be implemented by either a hardware configuration or a combined configuration of a hardware resource and software. As the software of the combined configuration, a program is used which is installed in a computer from a network or a computer-readable recording medium (or storage medium) in advance, and is executed by a processor of the computer, thereby realizing the functions of the respective devices by the computer.

Note that this invention is not limited to the embodiments described above, and can be embodied by modifying the components in an implementation stage without departing from the gist thereof. Further, various inventions can be formed by appropriate combinations of the plurality of components disclosed in the embodiments described above. For example, from among all components illustrated in the embodiments, several components may be deleted. Furthermore, components of different embodiments may be combined as appropriate.

Further, "and/or" means any one or more items of the items connected and listed by the "and/or" statement. As a specific example, "x and/or y" means any element of the set of three elements {(x), (y), (x, y)}. As another specific example, "x, y, and/or z" means any element of the set of seven elements {(x), (y), (z), (x, y), (x, z), z), (x, y, z)}.

Supplementary Note

An information processing device including:

an acquisition unit (151, 501) configured to acquire user data including at least one of vital data including biological information pertaining to a user and lifestyle data pertaining to the user;

a provision unit (155, 503, 504) configured to apply, to the user data, reference data indicating criteria for determining a content of the user data and, in accordance with a result of the reference data being thus applied, provide, to the user, coupon data pertaining to a coupon configured to encourage the user to take a specific action; and a determination unit (156, 506) configured to determine, on the basis of usage history data of the coupon data thus provided and the user data corresponding to the usage history data, whether or not a coupon corresponding to the usage history data is effective in improving a lifestyle of the user.

REFERENCE SIGNS LIST

100 Biological information acquisition device
101 Measurement unit
102 Storage unit
103 Transmission unit
104 Operation unit
105 Clocking unit
120 Mobile information terminal
121 Reception unit
122 Storage unit
123 Transmission unit
124 Control unit
125 Operation unit
126 Clocking unit
150 Information processing device
151 Reception unit
152 Lifestyle DB
153 Reference DB
154 Coupon DB
155 Provision unit
156 Determination unit
157 Usage history DB
158 Updating unit
159 Weight factor DB
211 Output device
212 Input device
213 Control unit
214 Storage unit
215 Drive
216 External interface
217 Communication interface
218 Power source
219 Clocking device
220 Vital DB
221 Lifestyle DB
222 Reference DB
223 Coupon DB
224 Usage history DB
225 Weight factor DB
311 Output device
312 Input device
313 Control unit
314 Storage unit
315 Drive
316 External interface
317 Communication interface
318 Battery
319 Clocking device
320 Imaging device
411 Output device
412 Input device
413 Control unit
414 Storage unit
415 Drive
416 External interface
417 Communication interface
418 Battery
419 Clocking device
420 Biometric sensor
421 Motion sensor
501 Reception unit
502 Retrieval unit
503 Selection unit
504 Provision unit
505 Usage status acquisition unit
506 Determination unit
507 Updating unit
508 Transmission unit
601 Reception unit
602 Image acquisition unit
603 Food analysis unit
604 Display control unit
605 Instruction reception unit
606 Transmission unit

The invention claimed is:

1. An information processing device comprising:
an acquisition unit configured to acquire user data including vital data including biological information pertaining to a user and lifestyle data pertaining to the user;
a provision unit configured to apply, to the user data, reference data indicating criteria for determining a content of the user data and, in accordance with a result of the reference data being thus applied, provide, to the user, coupon data pertaining to a coupon configured to encourage the user to take a specific action; and
a determination unit configured to determine, on the basis of usage history data of the coupon data thus provided and the user data corresponding to the usage history data, whether or not a coupon corresponding to the usage history data is effective in improving a lifestyle of the user, the usage history data indicating history data of the coupons used by the user,
wherein in a case where a plurality of coupons expected to be effective for the user are used, the determination unit is configured to determine whether or not mutual interaction needs to be considered when the coupons are used in combination, based on data that indicates whether or not there is interaction between coupons stored in advance.

2. The information processing device according to claim 1, further comprising:
an updating unit configured to update a weight factor indicating a degree of association between a coupon determined to be effective in improving a lifestyle and the vital data and the lifestyle data corresponding to the coupon by increasing the weight factor.

3. The information processing device according to claim 1, wherein
the determination unit is configured to determine that the coupon was effective in a case where a variation amount, varied to an amount reflecting an effect of improving a lifestyle, in an amount indicated by the vital data and the lifestyle data, before and after coupon use, is greater than a threshold value.

4. The information processing device according to claim 1, wherein
the vital data include at least one of blood pressure data, pulse data, body temperature data, weight data, and electrocardiogram data.

5. The information processing device according to claim 1, wherein
the lifestyle data include at least one of intake data indicating food consumed and an intake amount of food, exercise data indicating an exercise amount, sleep data indicating a sleep amount, smoking data indicating a smoking amount, medication data of medicine taken, food intake speed data indicating a speed of food intake, and periodontal disease data.

6. The information processing device according to claim 1, wherein
the reference data include data including one or more threshold values configured to give meaning to the user data.

7. The information processing device according to claim 2, wherein
the determination unit is configured to determine that the coupon was effective in a case where a variation amount, varied to an amount reflecting an effect of improving a lifestyle, in an amount indicated by the vital data and the lifestyle data, before and after coupon use, is greater than a threshold value.

8. The information processing device according to claim 2, wherein
the vital data include at least one of blood pressure data, pulse data, body temperature data, weight data, and electrocardiogram data.

9. The information processing device according to claim 3, wherein
the vital data include at least one of blood pressure data, pulse data, body temperature data, weight data, and electrocardiogram data.

10. The information processing device according to claim 2, wherein
the lifestyle data include at least one of intake data indicating food consumed and an intake amount of food, exercise data indicating an exercise amount, sleep data indicating a sleep amount, smoking data indicating a smoking amount, medication data of medicine taken, food intake speed data indicating a speed of food intake, and periodontal disease data.

11. The information processing device according to claim 3, wherein
the lifestyle data include at least one of intake data indicating food consumed and an intake amount of food, exercise data indicating an exercise amount, sleep data indicating a sleep amount, smoking data indicating a smoking amount, medication data of medicine taken, food intake speed data indicating a speed of food intake, and periodontal disease data.

12. The information processing device according to claim 4, wherein
the lifestyle data include at least one of intake data indicating food consumed and an intake amount of food, exercise data indicating an exercise amount, sleep data indicating a sleep amount, smoking data indicating a smoking amount, medication data of medicine taken, food intake speed data indicating a speed of food intake, and periodontal disease data.

13. The information processing device according to claim 2, wherein
the reference data include data including one or more threshold values configured to give meaning to the user data.

14. The information processing device according to claim 3, wherein
the reference data include data including one or more threshold values configured to give meaning to the user data.

15. The information processing device according to claim 4, wherein
the reference data include data including one or more threshold values configured to give meaning to the user data.

16. The information processing device according to claim 5, wherein
the reference data include data including one or more threshold values configured to give meaning to the user data.

17. A computer-implemented information processing method comprising:
acquiring user data including vital data including biological information pertaining to a user and lifestyle data pertaining to the user;
applying, to the user data, reference data indicating criteria for determining a content of the user data and, in accordance with a result of the reference data being thus applied, providing, to the user, coupon data pertaining to a coupon configured to encourage the user to take a specific action; and
determining, on the basis of usage history data of the coupon data thus provided and the user data corresponding to the usage history data, whether or not a coupon corresponding to the usage history data is effective in improving a lifestyle of the user, the usage history data indicating history data of the coupons used by the user,
wherein in a case where a plurality of coupons expected to be effective for the user are used, the determining step includes determining whether or not mutual interaction needs to be considered when the coupons are used in combination, based on data that indicates whether or not there is interaction between coupons stored in advance.

18. A non-transitory computer-readable storage medium storing a program executed by at least one processor to perform operations comprising:
acquiring user data including vital data including biological information pertaining to a user and lifestyle data pertaining to the user;
applying, to the user data, reference data indicating criteria for determining a content of the user data and, in accordance with a result of the reference data being thus applied, providing, to the user, coupon data pertaining to a coupon configured to encourage the user to take a specific action; and determining on the basis of usage history data of the coupon data thus provided and the user data corresponding to the usage history data, whether or not a coupon corresponding to the usage history data is effective in improving a lifestyle of the user, the usage history data indicating history data of the coupons used by the user, wherein in a case where a plurality of coupons expected to be effective for the user are used, the determining operation includes determining whether or not mutual interaction needs to be considered when the coupons are used in combination, based on data that indicates whether or not there is interaction between coupons stored in advance.

19. The non-transitory computer-readable storage medium according to claim 18, wherein the operations further comprise updating a weight factor indicating a degree of association between a coupon determined to be effective in improving a lifestyle and the vital data and/or the lifestyle data corresponding to the coupon by increasing the weight factor.

20. The non-transitory computer-readable storage medium according to claim 18, wherein the operations further comprise determining that the coupon is effective in a case where a variation amount, varied to an amount reflecting an effect of improving a lifestyle, in an amount indicated by the vital data and the lifestyle data, before and after coupon use, is greater than a threshold value.

* * * * *